US009011870B2

(12) United States Patent
Leenhouts et al.

(10) Patent No.: US 9,011,870 B2
(45) Date of Patent: Apr. 21, 2015

(54) BIFUNCTIONAL PROTEIN ANCHORS

(75) Inventors: Cornelis Johannes Leenhouts, Haren (NL); Maarten Leonardus Van Roosmalen, Groningen (NL); Tjibbe Bosma, Lippenhuizen (NL)

(73) Assignee: Applied Nanosystems B.V., Groningen (NL)

( * ) Notice: Subject to any disclaimer, the term of this patent is extended or adjusted under 35 U.S.C. 154(b) by 1841 days.

(21) Appl. No.: 11/989,118

(22) PCT Filed: Jul. 20, 2006

(86) PCT No.: PCT/NL2006/000382
§ 371 (c)(1),
(2), (4) Date: Mar. 25, 2008

(87) PCT Pub. No.: WO2007/011216
PCT Pub. Date: Jan. 25, 2007

(65) Prior Publication Data
US 2009/0263414 A1    Oct. 22, 2009

(30) Foreign Application Priority Data

Jul. 20, 2005    (EP) .................................. 050766880

(51) Int. Cl.
*A61K 39/385*    (2006.01)
*C07K 14/335*    (2006.01)
*A61K 39/00*    (2006.01)

(52) U.S. Cl.
CPC ..... *C07K 14/335* (2013.01); *A61K 2039/55555* (2013.01); *A61K 2039/6068* (2013.01); *A61K 2039/622* (2013.01); *C07K 2319/70* (2013.01); *C07K 2319/705* (2013.01)

(58) Field of Classification Search
None
See application file for complete search history.

(56) References Cited

U.S. PATENT DOCUMENTS

| | | | | |
|---|---|---|---|---|
| 6,114,147 | A * | 9/2000 | Frenken et al. | 435/69.7 |
| 6,896,887 | B2 * | 5/2005 | Leenhouts et al. | 424/234.1 |
| 7,067,639 | B2 * | 6/2006 | Leenhouts et al. | 530/412 |
| 7,169,383 | B1 * | 1/2007 | Buist et al. | 424/93.1 |
| 7,312,311 | B2 * | 12/2007 | Buist et al. | 530/350 |
| 7,541,039 | B2 * | 6/2009 | Leenhouts et al. | 424/234.1 |
| 7,858,357 | B2 * | 12/2010 | Leenhouts et al. | 435/243 |
| 8,142,789 | B2 * | 3/2012 | Leenhouts et al. | 424/190.1 |
| 2003/0180816 | A1 * | 9/2003 | Leenhouts et al. | 435/7.22 |
| 2005/0169937 | A1 * | 8/2005 | Buist et al. | 424/190.1 |
| 2009/0239264 | A1 * | 9/2009 | Leenhouts et al. | 435/71.2 |
| 2009/0263414 | A1 * | 10/2009 | Leenhouts et al. | 424/194.1 |
| 2011/0044982 | A1 * | 2/2011 | Leenhouts et al. | 424/133.1 |
| 2014/0093532 | A1 * | 4/2014 | Leenhouts et al. | 424/192.1 |

FOREIGN PATENT DOCUMENTS

| | | | |
|---|---|---|---|
| EP | 1746103 | A1 * | 1/2007 |
| EP | 2168987 | A1 * | 3/2010 |
| JP | 2002284798 | | 10/2002 |
| WO | WO 94/18330 | A1 * | 8/1994 |
| WO | WO 99/25836 | * | 5/1999 |
| WO | WO 99/25836 | A1 * | 5/1999 |
| WO | WO 02/10126 | | 2/2002 |
| WO | WO 02/101026 | | 12/2002 |
| WO | WO 2004/102199 | A2 | 11/2004 |
| WO | WO 2010/033031 | A1 * | 3/2010 |
| WO | WO 2011/040811 | A1 * | 4/2011 |

OTHER PUBLICATIONS

Raha et al, Appl. Microbiol. Biotechnol., 2005, 68:75-81.*
Audouy et al, Vaccine, 2007, 25:2497-2506.*
Bosma et al, Appl. and Environ. Microbiol., Jan. 2006, 72/1:880-889.*
Maraffini et al, MMicrobiology and Molecular Biology Reviews, Mar. 2006, 70/1:192-221.*
Ramasamy et al, Vaccine, 2006, 24:3900-3908.*
van Roosmalen et al, Methods, 2006, 38:144-149.*
Bateman et al, J. Mol. Biol., 2000, 299:1113-1119.*
Raha et al., Cell surface display system for *Lactococcus lactis*: a novel development for oral vaccine, Applied Microbiology and Biotechnology, vol. 68, No. 1, Jul. 2005, pp. 75-81 (Abstract).
Van Roosmalen et al., Mucosal vaccine delivery of antigens tightly bound to an adjuvant particle made from food-grade bacteria, Methods: A Companion to Methods in Enzymology, Academic Press, Inc., New York, NY, US., vol. 38, No. 2, Feb. 2006, pp. 144-149 (Abstract).
PCT International Search Report, PCT/NL2006/000382 dated Jan. 8, 2007.
PCT International Preliminary Report on Patentability, PCT/NL2006/000382, dated Aug. 6, 2007.

* cited by examiner

*Primary Examiner* — Nita M Minnifield
(74) *Attorney, Agent, or Firm* — TraskBritt, P.C.

(57) ABSTRACT

The invention relates to the areas of immunology and vaccine delivery. More specifically, it relates to a bacterial vaccine delivery technology with built-in immunostimulatory properties which allows the immobilization of any antigen of interest, without prior antigen modification. Provided is an antigen-loaded immunogenic carrier complex comprising at least one bifunctional polypeptide attached to an immunogenic carrier, said bifunctional polypeptide comprising a peptidoglycan binding domain (PBD) through which the polypeptide is attached to said carrier, fused to an antigen binding domain (ABD) to which at least one antigen of interest is bound. Also provided is a pharmaceutical (e.g. vaccine) composition comprising an antigen-loaded immunogenic carrier complex of the invention.

19 Claims, 5 Drawing Sheets

BIFUNCTIONAL PROTEIN ANCHORS

Figure 1:
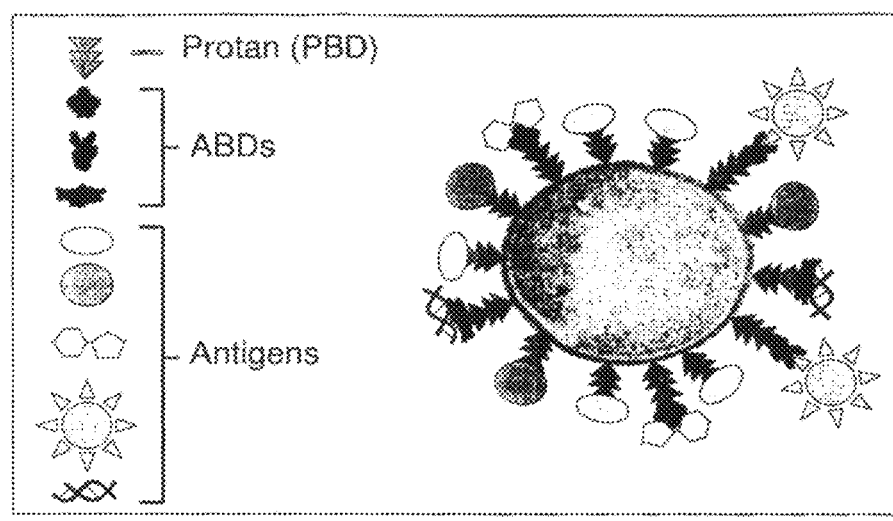

The invention relates to the areas of immunology and vaccine delivery. More specifically, it relates to a bacterial vaccine delivery technology with built-in immunostimulatory properties, which allows the immobilization of any antigen of interest, without prior antigen modification.

Vaccine delivery or immunisation via attenuated bacterial vector strains expressing distinct antigenic determinants against a wide variety of diseases is now commonly being developed. Mucosal (for example nasal or oral) vaccination using such vectors has received a great deal of attention. For example, both systemic and mucosal antibody responses against an antigenic determinant of the hornet venom were detected in mice orally colonised with a genetically engineered human oral commensal *Streptococcus gordonii* expressing said antigenic determinant on its surface (Medaglini et al., PNAS 1995, 2; 6868-6872).

Also, a protective immune response could be elicited by oral delivery of a recombinant bacterial vaccine wherein tetanus toxin fragment C was expressed constitutively in *Streptococcus lactis* (Robinson et al., Nature Biotechnology 1997, 15; 653-657). Especially mucosal immunisation as a means of inducing IgG and secretory IgA antibodies directed against specific pathogens of mucosal surfaces is considered an effective route of vaccination. Immunogens expressed by bacterial vectors are presented in particulate form to the antigen-presenting cells (for example M-cells) of the immune system and should therefore be less likely to induce tolerance than soluble antigens. In addition, the existence of a common mucosal immune system permits immunisation on one specific mucosal surface to induce secretion of antigen-specific IgA, and other specific immune responses at distant mucosal sites. A drawback to this approach is the potential of the bacterial strain to cause inflammation and disease in itself, potentially leading to fever and bacteraemia. An alternative approach avoids the use of attenuated bacterial strains that may become pathogenic themselves by choosing recombinant commensal bacteria as vaccine carriers, such as *Lactobacillus* ssp. and *Lactococcus* ssp.

However, a drawback of the use of such recombinant organisms is that they may colonise the mucosal surfaces, thereby generating a long term exposure to the target antigens expressed and released by these recombinant micro-organisms. Such long term exposure can cause immune tolerance. In addition, the mere fact alone that such organisms are genetically modified and contain recombinant nucleic acid(s) is meeting considerable opposition from the (lay) public as a whole, stemming from a low level of general acceptance for products containing recombinant DNA or RNA. Similar objections exist against the use of (even attenuated) strains of a pathogenic nature or against proteins or parts of proteins derived from pathogenic strains.

As explained above, commonly used techniques of heterologous surface display of proteins in general entail the use of anchoring or targeting proteins that are specific and selective for a limited set of micro-organisms which in general are of recombinant or pathogenic nature, thereby greatly restricting their potential applications.

We previously addressed this issue in patent applications WO 99/25836 and WO 02/101026, which describe the use of a chimeric fusion protein containing an AcmA(-like) binding domain fused to an antigen to attach antigens to non-viable spherical peptidoglycan particles derived from non-recombinant Gram-positive bacteria. The Gram-positive bacteria receive a non-enzymatic pretreatment (see WO 02/101026) before they are formulated with the antigens. The peptidoglycan particles, previously referred to as 'ghosts', still contain bacterial components, like peptidoglycan, which have immunostimulatory properties. Accordingly, these particles are now referred to as Gram-positive Enhancer Matrix ("GEM") or "GEM particles".

Thus, the methods disclosed in WO 99/25836 and WO 02/101026 avoid the use of live bacteria and/or of microorganisms which in general are of recombinant or pathogenic nature. However, these previously disclosed methods are limited to the attachment of proteinaceous antigens that can be produced (recombinantly) as a chimeric proteinaceous product. For some protein antigens this may not be a feasible approach. There may for instance be specific requirements for the production of the antigen in which the presence of an AcmA(-like) binding domain, can interfere. In addition, for non-proteinaceous antigens a genetic fusion can of course not be made. Also, the method does not allow the attachment of particulate antigens. It can be envisaged to couple an antigen of interest covalently by chemical means to a peptidoglycan particle, for instance using a chemical cross-linker reactive with both the antigen and the bacterial particle. The peptidoglycan layer of the cell wall of lactic acid bacteria is covered by a variety of substances, for example (lipo)teichoic acids, neutral and acidic polysaccharides, and (surface) proteins. However, this chemical approach may not be suitable for every type of antigen since chemical modification can interfere with antigen efficacy to induce the immune system. Furthermore, most chemical crosslinkers require a specific reactive group (e.g. SH) to mediate a covalent interaction, which group may not always be present or which may be located at an undesirable (e.g. antigen binding) site within the molecule(s) cross-linked.

It is a goal of the present invention to overcome these limitations. To that end, bifunctional polypeptides were developed that contain a functionality to bind (non-covalently) an antigen of interest as well as a functionality to bind (non-covalently) an immunogenic carrier, such as a GEM particle. This system allows the immobilization of any antigen of interest, without prior modification, on the surface of GEM particles. The antigens can be (poly)peptides, carbohydrates, lipids, DNA, RNA or any other bio-organic compound and can even have a particulate nature by themselves, e.g. viral particles.

Therefore, the invention relates to an antigen-loaded immunogenic carrier complex comprising at least one polypeptide attached to an immunogenic carrier, said polypeptide comprising a peptidoglycan binding domain (PBD) through which the polypeptide is attached to said carrier, fused to an antigen binding domain (ABD) capable of binding an antigen of interest. In an antigen-loaded complex of the invention, at least one antigen of interest is bound (non-covalently) to said ABD. The PBD comprises an amino acid sequence capable of binding to peptidoglycan, which sequence is selected from the group consisting of (i) a LysM domain, (ii) an amino acid sequence retrieved from a homology search in an amino acid sequence database with one of the three LysM domains (repeated regions) in the C-terminus of *Lactococcus lactis* cell wall hydrolase AcmA (said domains herein also referred to as AcmA LysM domains) and (iii) a sequence showing at least 70% identity to any one of the three AcmA LysM domains.

The PBD is capable of attaching to the cell wall of a Gram-positive microorganism. The term "antigen binding" is meant to indicate the capacity to bind an antigen of interest. Said capacity is conferred by at least one bifunctional polypeptide. The term "bifunctional" indicates that the polypeptide has at least two different functionalities: a peptidoglycan binding functionality and an antigen binding functionality. The functionalities can be multivalent, e.g. a bifunctional polypeptide may comprise multiple antigen binding sites.

The term "immunogenic carrier" refers to a moiety which, upon administration to a subject, has the capacity to enhance or modify the immune-stimulating properties of an antigen attached to it. An immunogenic carrier thus has adjuvant properties. Furthermore, it comprises peptidoglycans to allow attachment of one or more bifunctional linker polypeptide(s) via its peptidoglycan binding domain (PBD). Non-recombinant immunogenic carriers are preferred for reasons given above.

In a preferred embodiment, the immunogenic carrier complex is a non-viable spherical peptidoglycan particle obtained from a Gram-positive bacterium (GEM particle, or "ghost"). Methods for the preparation of GEM particles have been described before, for instance in patent applications WO 02/101026 and WO 2004/102199. The process preserves most of the bacteria's native spherical structure. Briefly, the method comprises treating Gram-positive bacteria with a solution capable of removing a cell-wall component, such as a protein, lipoteichoic acid or carbohydrate, from the cell-wall material. The resulting GEM particles may be subsequently stored until it is contacted with a desired bifunctional polypeptide. GEM particles bind substantially higher amounts of a PBD fusion than untreated Gram-positive bacteria. Therefore, a high loading capacity can be achieved for antigens on GEM particles (WO 02/101026). GEM particles are also better able to bind to and/or are more easily taken up by specific cells or tissues than mechanically disrupted cell-wall material. The ability of GEM particles to target macrophages or dendritic cells enhances their functional efficacy. The non-recombinant, non-living immunogenic carrier complex of the present invention is therefore well suited as a vaccine delivery vehicle. See also WO 02/101026 and WO2004/102199.

In one embodiment the invention provides a vaccine delivery technology, which is based on GEM particles with one or more antigens attached to the particles through the use of bifunctional polypeptides, wherein the GEM particles serve as immunogenic backbone to surface attach compounds of pathogenic origin, thereby mimicking a pathogenic particle (FIG. 1). This delivery technology can mimic a pathogen by delivering subunit vaccines as a particle to the immunoreactive sites.

The GEM particles can in principle be prepared from any Gram-positive bacterium. The cell walls of Gram-positive bacteria include complex networks of peptidoglycan layers, proteins, lipoteichoic acids and other modified carbohydrates. Chemical treatment of the bacterial cell-wall material may be used to remove cell-wall components such as proteins and lipoteichoic acids to result in GEM particles with improved binding characteristics. Preferably, an antigen binding immunogenic carrier complex of the invention comprises GEM particles obtained using an acid solution (see e.g. WO 02/101026).

In a preferred embodiment, the immunogenic carrier complex is prepared from a non-pathogenic bacterium, preferably a food-grade bacterium or a bacterium with the G.R.A.S. (generally-recognized-as-safe) status. In one embodiment, the cell-wall material is derived from a *Lactococcus*, a *Lactobacillius*, a *Bacillus* or a *Mycobacterium* ssp. Use of a Gram-positive, food-grade bacterium, such as *Lactococcus lactis*, offers significant advantages over use of other bacteria, such as *Salmonella* or *Mycobacterium*, as a vaccine delivery vehicle. *L. lactis* does not replicate in or invade human tissues and reportedly possesses low intrinsic immunity (Norton et al. 1994). *L. lactis* expressing tetanus toxin fragment C has been shown to induce antibodies after mucosal delivery that protect mice against a lethal challenge with tetanus toxin even if the carrier bacteria were killed prior to administration (Robinson et al. 1997). In contrast to the non-recombinant GEM particles in an immunogenic carrier complex disclosed herein, these bacteria still contain recombinant DNA that will be spread into the environment, especially when used in wide-scale oral-immunization programmes. This uncontrollable shedding of recombinant DNA into the environment may have the risk of uptake of genes by other bacteria or other (micro) organisms.

A polypeptide of the invention comprises a peptidoglycan binding domain (PBD) which allows for the attachment of any antigen of interest to an immunogenic carrier, such as a GEM. In one embodiment, the PBD comprises an amino acid sequence capable of binding to peptidoglycan, which sequence is a LysM domain. Preferably, a polypeptide comprises at least two, more preferably at least three LysM domains. The LysM (lysin motif) domain is about 45 residues long. It is found in a variety of enzymes involved in bacterial cell wall degradation (Joris et al., FEMS Microbiol Lett 1992; 70:257-264). The LysM domain is assumed to have a general peptidoglycan binding function. The structure of this domain is known ("The structure of a LysM domain from *E. coli* membrane-bound lytic murein transglycosylase D (MltD)". Bateman A, Bycroft M; J Mol Biol 2000; 299:1113-11192). The presence of the LysM domains is not limited to bacterial proteins. They are also present in a number of eukaryotic proteins, whereas they are lacking in archaeal proteins. A cell wall binding function has been postulated for a number of proteins containing LysM domains. Partially purified muramidase-2 of *Enterococcus hirae*, a protein similar to AcmA and containing six LysM domains, binds to peptidoglycan fragments of the same strain. The p60 protein of *Listeria monocytogenes* contains two LysM domains and was shown to be associated with the cell surface. The γ-D-glutamate-meso-diaminopimelate muropeptidases LytE and LytF of *Bacillus subtilis* have three and five repeats, respectively, in their N-termini and are both cell wall-bound.

A skilled person will be able to identify a LysM domain amino acid sequence by conducting a homology-based search in publicly available protein sequence databases using methods known in the art. A variety of known algorithms are disclosed publicly and a variety of publicly and commercially available software can be used. Examples include, but are not limited to MacPattern (EMBL), BLASTP(NCBI), BLASTX (NCBI) and FASTA (University of Virginia). In one embodiment, PFAM accession number PF01476 for the LysM domain (see World Wide Web.sanger.ac.uk/cgi-bin/Pfam/getacc?PF01476) is used to search for an amino acid sequence which fulfils the criteria of a LysM domain. The PFAM website provides two profile hidden Markov models (profile HMMs) which can be used to do sensitive database searching using statistical descriptions of a sequence family's consensus. HMMER is a freely distributable implementation of profile HMM software for protein sequence analysis.

The C-terminal region of the major autolysin AcmA of *L. lactis* contains three homologous LysM domains, which are separated by nonhomologous sequences. For the amino acid sequences of the three AcmA LysM domains see for example FIG. 10 of WO99/25836 wherein the three LysM domains are indicated by R1, R2 and R3. The C-terminal region of AcmA was shown to mediate peptidoglycan binding of the autolysin (Buist et al. [1995] J. Bacteriol. 177:1554-1563). In one embodiment, an antigen binding immunogenic carrier complex of the invention comprises a bifunctional polypeptide bound via its PBD to a peptidoglycan at the surface of the immunogenic carrier, preferably a GEM particle, wherein said PBD comprises at least one LysM domain as present in AcmA. Variations within the exact amino acid sequence of an AcmA LysM domain are also comprised, under the provision that the peptidoglycan binding functionality is maintained. Thus, amino acid substitutions, deletions and/or insertions may be performed without losing the peptidoglycan binding capacity. Some parts of the AcmA LysM domains are less suitably varied, for instance the conserved GDTL and GQ motifs found in all three domains. Others may however be altered without affecting the efficacy of the PBD to bind the immunogenic carrier. For example, amino acid residues at positions which are of very different nature (polar, apolar, hydrophilic, hydrophobic) amongst the three LysM domains of AcmA can be modified. Preferably, the PBD comprises a sequence that is at least 70%, preferably 80%, more preferably 90%, like 92%, 95%, 97% or 99%, identical to one of the three LysM domains of *L. lactis* AcmA. The PBD of a polypeptide for use in the present invention may contain one or more of such (homologous) AcmA LysM domains, either distinct or the same. Typically, the LysM domains are located adjacent to each other, possibly separated by one or more amino acid residues. The LysM domains can be separated by a short distance, for example 1-15 amino acids apart, or by a medium distance of 15-100 amino acids, or by a large distance, like 150 or even 200 amino acids apart.

In a certain aspect, the invention concerns a PBD, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an AcmA LysM domain.

The "percentage of amino acid sequence identity" for a polypeptide, such as 70, 80, 90, 95, 98, 99 or 100 percent sequence identity may be determined by comparing two optimally aligned sequences over a comparison window, wherein the portion of the polypeptide sequence in the comparison window may include additions or deletions (i.e. gaps) as compared to the reference sequence (which does not comprise additions or deletions) for optimal alignment of the two amino acid sequences. The percentage is calculated by: (a) determining the number of positions at which the identical amino acid occurs in both sequences to yield the number of matched positions; (b) dividing the number of matched positions by the total number of positions in the window of comparison; and (c) multiplying the result by 100 to yield the percentage of sequence identity. Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al. 1990. J. Mol. Biol. 215:403; Altschul, S. F. et al. 1997. Nucleic Acid Res. 25:3389-3402) and ClustalW programs both available on the internet.

In another embodiment, a PBD comprises a LysM domain which is present in an amino acid sequence retrieved from a homology search in an amino acid sequence database with an AcmA LysM domain, wherein the LysM domain is capable of attaching the substance to the cell wall of a Gram-positive microorganism. Preferably, the amino acid sequence retrieved is an amino acid sequence originating from a Gram-positive bacterium. It is for instance an amino acid sequence of a bacterial cell wall hydrolase. Preferably, the retrieved amino acid sequence shows at least 70%, more preferably 80%, most preferably at least 90% sequence identity with an AcmA LysM domain. Examples of sequences that may be retrieved can be found in FIG. 11 of patent application WO99/25836.

As will be clear from the above, a PBD can be structurally defined in various manners. However, in all cases a PBD can be defined as a means for binding to the cell wall of a microorganism, wherein said means for binding is of peptidic nature. In one embodiment, the PBD is capable of binding to a Gram-positive bacterium or cell wall material derived thereof (e.g. a GEM particle). The binding capacity of a PBD can be readily determined in a binding assay comprising the steps of labeling the PBD with a reporter molecule, contacting the labeled PBD with a Gram-positive micro-organism to allow for binding of said means to said micro-organism; and determining the binding capacity of said PBD by detecting the absence or presence of reporter molecule associated with the micro-organism.

The reporter molecule, also referred to as detectable molecule, for use in the binding assay can be of various nature. Many types of reporter molecules are known in the art. It is for example a fluorescent molecule (e.g. FITC), an antigen, an affinity tag (e.g. biotin) an antibody or an enzyme. A reporter molecule can be conjugated to the PBD by methods known in the art. In case the reporter molecule is of peptidic nature, the step of labeling the PBD with a reporter molecule preferably comprises the generation of a genetic fusion between the PBD and reporter molecule. Such fusions have been described in the art. For example, WO99/25836 describes the generation of fusion constructs between a polypeptide comprising zero, one, two or three AcmA LysM domains and a reporter enzyme (in that case either α-amylase or β-lactamase). To determine whether a given polypeptide is a PBD of the present invention, a person skilled in the art will be able to apply standard recombinant DNA techniques to provide a fusion with a reporter polypeptide (enzyme, antigen or the like) which can subsequently be tested for cell binding activity.

Preferred enzyme reporter molecules are those that allow for calorimetric or fluorescent detection of their activity. Many reporter enzyme systems are described in the art which make use of colorimetric or fluorimetric substrates, like horseradish peroxidase (HRP)/2,2'-azino-bis(3-ethylbenzthiazoline-6-sulphonic acid) (ABTS); alkaline phosphatase/ 4-nitro phenylphosphate or beta-galactosidase/2-nitrophenyl-beta-D-galactopyranoside (2-NPG).

In case the PBD is labelled with an antigen, determining the binding capacity of said PBD by detecting the absence or presence of reporter molecule associated with the microorganism typically comprises the use of an antibody (e.g. a monoclonal murine antibody) specifically reactive with the antigen. The antigen-antibody complex can be detected using a secondary antibody (e.g. rabbit anti-mouse IgG antibody) carrying a detectable label in a so-called sandwich format. The secondary antibody is for instance provided with a reporter enzyme whose activity can be measured using a colorimetric substance mentioned above. It is also possible to label the PBD with a primary antibody as reporter molecule and detect the absence or presence of reporter molecule associated with the micro-organism using a secondary antibody carrying a detectable label (enzyme, fluorochrome).

A Gram-positive microorganism for use in a binding assay can be viable or non-viable. Included are Gram-positive bacteria, such as a *Bacillus* ssp., *Streptococcus* ssp., *Mycobacterium* ssp., *Listeria* ssp. or a *Clostridium* ssp. The step of contacting the labeled PBD with a Gram-positive micro-organism to allow for binding of said means to said microorganism can involve the resuspension of a pelleted culture of exponentially growing Gram-positive bacteria, like *L. lactis*, in a solution comprising the labelled PBD or a crude cell extract containing the labeled PBD. Said solution can also be a culture supernatant of a host cell expressing and secreting the labeled PBD. Following a certain period of incubation, for instance 1-120 min at 4-40° C., like 1-30 min. at 10-40° C., the Gram-positive bacteria are pelleted and washed to remove any non-specifically bound reporter molecule. Thereafter, the amount of reporter molecule associated with the pelleted bacteria is determined.

In a specific embodiment, a cell binding assay comprises the use of α-amylase from *Bacillus lichenifomis* or *E. coli* TEM β-lactamase as reporter molecule as a fusion to PBD. Fusion proteins are recombinantly produced in a bacterial host cell which secretes the fusion protein in the culture supernatant. GEM particles are be used as Gram-positive microorganism in the binding assay. They can be prepared as described in WO 02/101026 and herein below. GEM particles loaded with both fusion proteins were spun down and washed twice with PBS. Enzyme activity of bound α-amylase—and β-lactamase PBD fusions are measured colorimetrically. α-Amylase activity is determined by incubating the loaded GEM particles in 1 ml amylose azure (Sigma) substrate solution (0.6 mg/ml amylose azure in 20 mM $K_2HPO_4/KH_2PO_4$-buffer, 50 mM NaCl, pH 7.5), at 37° C. and 200 rpm. After 60 min, GEM particles and insoluble amylose azure were spun down, and the absorbance at 595 nm was measured. β-Lactamase activity was measured by adding 40 μl nitrocefin (CalBiochem) to GEM particles loaded with β-lactamase PBD fusion in a final volume of 1 ml PBS. After 30 min the absorbance at 486 nm was measured.

A polypeptide comprising a PBD and an ABD wherein the PBD comprises the three LysM domains of *L. lactis* cell wall hydrolase AcmA, also referred to as cA or protein anchor in WO 99/25836 and WO 02/101026, will herein be termed "Protan linker". As will be understood by the skilled person, the Protan linker may contain one or more amino acid substitutions as compared to the naturally occurring AcmA LysM sequences, provided that the peptidoglycan binding capacity is maintained.

The relative positions of the ABD and the PBD within the polypeptide can vary. However, it will be understood that allowing attachment of the polypeptide to the immunogenic carrier via the PBD on the one hand and binding of an antigen via the ABD on the other hand requires a certain degree of spacing between the domains to avoid or minimize mutual interference. In a preferred embodiment, a polypeptide of the invention comprises a PBD fused via a linker or spacer sequence to an ABD. Said linker or spacer can be a relatively short stretch of amino acids, e.g. 1-200, a medium size linker, e.g. 200-600 amino acids, or a larger linker, of more than 600 residues. For example, in one embodiment the N-terminal part of the polypeptide comprises a PBD which is fused via a linker to an ABD located in the C-terminal part. In another embodiment, the PBD constitutes the C-terminal part of the polypeptide and the ABD the N-terminal part. The ABD and/or PBD do not have to reside at the extreme ends of the polypeptides; one or more amino acid residues can be present at either end of the polypeptide which are neither part of the ABD nor of the PBD.

A polypeptide of the invention comprises one or more antigen binding domains (ABDs). A multiplicity of ABDs within a single polypeptide allows the presentation of an antigen on an immunogenic carrier complex at a high density. In one embodiment, a polypeptide comprises two ABDs, capable of binding either the same or distinct antigens of interest. If multiple ABDs are present, it may be advantageous to place them adjacent to each other, e.g. with one or more amino acids in between to allow for an optimal binding of the multiple antigens to the polypeptide.

An ABD present in a polypeptide of the invention is a proteinaceous moiety capable of binding to an antigen of interest. Any type of antigen can be bound to an antigen binding immunogenic carrier complex of the invention, provided that there is a suitable ABD available. The antigen of interest can be selected from the group consisting of polypeptides, carbohydrates, lipids, polynucleotides and pathogenic antigens, including inactivated viral particles and purified antigenic determinants. In one embodiment, an antigen of interest is an antigen which cannot be produced as a fusion to a PBD, like an antigen comprising at least one non-proteinaceous moiety.

In one embodiment, the antigen of interest is a polynucleotide. Immunization with polynucleotides is a recent development in vaccine development. This technology has been referred to as genetic immunization or DNA immunization. The basis for this approach to immunization is that cells can take-up plasmid DNA and express the genes within the transfected cells. Thus, the vaccinated animal itself acts as a bioreactor to produce the vaccine. This makes the vaccine relatively inexpensive to produce. Some of the advantages of polynucleotide immunization is that it is extremely safe, induces a broad range of immune responses (cellular and humoral responses), long-lived immunity, and, most importantly, can induce immune responses in the presence of maternal antibodies. Although this is one of the most attractive developments in vaccine technology, there is a great need to develop better delivery systems to improve the transfection efficiency in vivo. In a specific aspect of the invention, an immunogenic carrier complex of the invention is used to deliver dsRNA, for example in an RNA interference (RNAi)-based therapy. Such therapy is particularly suitable to combat viral infections.

It will be understood that the structural characteristics of an ABD will primarily depend on the antigen of interest. Known binding partners of an antigen of interest, or a part of such known binding partner, may be used as ABD. For example, the capacity of the polypeptide to bind a pathogen, e.g. virus or bacterium, may be conferred by using a normal host receptor for the pathogen. Pathogen host receptors are known in the art and their sequences have been determined and stored in publicly available databases. For example, ICAM-1 is a host receptor for human rhinovirus (HRV) and CD4 for HIV.

In another aspect, the ABD comprises an antibody or functional fragment thereof, e.g. a Fab fragment, containing the antigen binding site, or other polypeptide, that binds to an antigen of interest. Many specific antibody (fragments)

known in the art can be used in the present invention. For instance, an antibody (fragment) that binds to a conserved determinant on the viral surface, such as VP4 on poliovirus, or gp120 on HIV, or HA on influenza virus. Industrial molecular affinity bodies (iMab®) are also suitably used as ABD according to the invention (see e.g. WO2004108749 from CatchMabs BV, The Netherlands). Nanobodies™ developed by Ablynx, Gent, Belgium may also be used.

WO 02/101026 in the name of the applicant discloses the use of GEM particles as delivery vehicles for a polypeptide fusion between an AcmA-type protein anchor and a reactive group, like proteins, peptides and antibodies. Therein, the antibodies do not serve as carrier for an antigen but they are therapeutic substances themselves i.e. through specific interaction with endogenous antigens. Of course, for that purpose the antibody must not be "pre-loaded" with antigen, as is the case in the present invention. WO 02/101026 therefore does not disclose or suggest the loading of a antibodies attached to GEM-particles with antigen of interest.

Antibody fragments and peptides specific for essentially any antigen, be it a peptide, sugar, lipid, nucleic acid or whole organism etc., can be selected by methods known in the art. Peptide libraries containing large amounts of randomly synthesized peptides which can be used in selecting a suitable binding partner for an antigen of interest are commercially available. For instance, New England Biolabs offers pre-made random peptide libraries, as well as the cloning vector M13KE for construction of custom libraries. The pre-made libraries consist of linear heptapeptide and dodecapeptide libraries, as well as a disulfide-constrained heptapeptide library. The randomized segment of the disulfide-constrained heptapeptide is flanked by a pair of cysteine residues, which are oxidized during phage assembly to a disulfide linkage, resulting in the displayed peptides being presented to the target as loops. All of the libraries have complexities in excess of 2 billion independent clones. The randomized peptide sequences in all three libraries are expressed at the N-terminus of the minor coat protein pIII, resulting in a valency of 5 copies of the displayed peptide per virion. All of the libraries contain a short linker sequence (Gly-Gly-Gly-Ser) between the displayed peptide and pIII.

Of particular interest is the use of phage display technology. Many reviews on phage display are available, see for example Smith and Petrenko [1997] Chem. Rev. 97:391-410. Briefly, phage display technology is a selection technique in which a library of variants of a peptide or human single-chain Fv antibody is expressed on the outside of a phage virion, while the genetic material encoding each variant resides on the inside. This creates a physical linkage between each variant protein sequence and the DNA encoding it, which allows rapid partitioning based on binding affinity to a given target molecule (antibodies, enzymes, cell-surface receptors, etc.) by an in vitro selection process called panning. In its simplest form, panning is carried out by incubating a library of phage-displayed peptides with a plate (or bead) coated with the target (i.e. antigen of interest), washing away the unbound phage, and eluting the specifically bound phage. The eluted phage is then amplified and taken through additional binding/amplification cycles to enrich the pool in favour of binding sequences. After 3-4 rounds, individual clones are typically characterized by DNA sequencing and ELISA. The DNA contained within the desired phage encoding the particular peptide sequence can then be used as nucleic acid encoding an ABD in a nucleic acid construct encoding a polypeptide of the invention.

There are several examples in the art of successful applications of phage display technology to identify peptides that bind selectively to micro-organisms. These teachings can be used to identify a peptide which can be used as antigen binding domain according to the present invention. For example, Knurr et al. (Appl. Environ Microbiol. 2003 November; 69(11):6841) describe the screening of phage display peptide libraries for 7- and 12-mer peptides that bind tightly to spores of *B. subtilis* and closely related species.

Lindquist et al. (Microbiology. 2002 February; 148(Pt 2):443-51) used a phage-displayed human single-chain Fv antibody library to select binding partners specific to components associated with the surface of *Chlamydia trachomatis* elementary bodies (EBs). While phage display has been used in the art primarily to select specific antibodies for purified components, these data show that this technology is suitable for selection of specific probes from complex antigens such as the surface of a microbial pathogen.

As another useful example, JP2002284798 discloses peptides, obtained by phage display technology, that bind specifically to influenza virus/hemaglutinin (HA). Also of particular interest for the present invention is a recent study by Kim et al. (J. Biochem Biophys Res Commun. 2005 Apr. 1; 329(1):312) which describes the screening of LPS-specific peptides from a phage display library using epoxy beads. LPS (lipopolysaccharide; endotoxin) is the major surface-exposed structural component of the outer membrane of Gram-negative bacteria. Its structure can be divided into three regions: (1) a phospholipids (lipid A) that is responsible for most of its biological activities, (2) a core oligosaccharide, and (3) an O-specific chain, which is an antigenic polysaccharide composed of a chain of highly variable repeating oligosaccharide subunits.

Kim et al., using biopanning on LPS-conjugated epoxy beads, repeatedly enriched clones encoding AWLPWAK (SEQ ID NO: 1) and NLQEFLF (SEQ ID NO: 2). These peptides were found to interact with the polysaccharide moiety of LPS, which is highly variable among Gram-negative bacterial species. In addition, it was found that phages encoding these peptides preferentially bound to the LPS of *Salmonella* family. AWLPWAK (SEQ ID NO: 1)-conjugated beads could be used to absorb *Salmonella enteritidis* from solution.

Whereas the present invention allows the immobilization of unmodified antigens to an immunogenic carrier, it is not restricted to unmodified antigens. In one embodiment of the invention, the ABD is capable of binding to an antigen of interest through a (chemical) modified or tagged version of the antigen of interest. For instance, an antigen can be provided with an affinity tag, which tag can be bound to the ABD. Example 2 herein below shows the binding of a biotin-tagged enzyme to GEM particles by virtue of a bifunctional Streptavidin-Protan bifunctional linker.

Also provided herein is a method for providing an antigen binding immunogenic carrier complex according to the invention. As is exemplified below, such a method comprises the steps of providing an immunogenic carrier, providing a polypeptide comprising a peptidoglycan binding domain (PBD) fused to an antigen binding domain (ABD), and allowing the attachment of said polypeptide to said immunogenic carrier to yield an antigen binding immunogenic carrier complex. As already indicated above, the use of phage display technology is particularly useful to obtain an ABD for a particular antigen of interest. Use can be made of commercial peptide or antibody fragment libraries.

The bifunctional polypeptide comprising an ABD and an PBD can be readily made by constructing a genetic fusion of the respective domains, typically spaced by a linker sequence, and expressing the gene in a suitable (bacterial) host cell employing methods well known in the art. As is exemplified in the Examples below, the recombinantly obtained polypeptide can be simply contacted with the immunogenic carrier to allow binding of the bifunctional polypeptide to peptidoglycans at the surface of the particles resulting in the antigen binding immunogenic carrier complex. In a specific aspect, the step of providing an immunogenic carrier comprises the preparation of non-viable spherical peptidoglycan particles from a Gram-positive bacterium (GEM particles).

The resulting carrier complex is contacted with one or more (modified) antigen(s) of interest to provide an antigen-loaded immunogenic carrier complex according to the invention wherein at least one antigen of interest is bound to an ABD. It is however also possible to reverse the order of binding, i.e. bind an antigen of interest to a polypeptide via its ABD prior to attaching the antigen-loaded polypeptide(s) via the PBD to the immunogenic carrier.

In one embodiment, the invention provides a pharmaceutical composition comprising an antigen-loaded immunogenic carrier complex according to the invention. For example, it provides an immunogenic composition comprising an antigen-loaded immunogenic carrier complex. An immunogenic composition is capable of inducing an immune response in an organism. In one embodiment, the immunogenic composition is a vaccine composition capable of inducing a protective immune response in an animal. The immunogenic composition, e.g. the vaccine, may be delivered to mucosal surfaces instead of being injected since mucosal surface vaccines are easier and safer to administer. A L. lactis derived immunogenic carrier complex may be used for mucosal vaccination since this bacterium is of intestinal origin and no adverse immune reactions are generally expected from L. lactis. Also provided is the use of an antigen binding immunogenic carrier complex according to the invention for the delivery of an (protective) antigen of interest to the immune system of a subject. The antigen binding immunogenic carrier complex comprises at least one bifunctional polypeptide attached to an immunogenic carrier, said polypeptide comprising a peptidoglycan binding domain (PBD) through which the polypeptide is attached to said carrier, fused to an antigen binding domain (ABD) capable of binding said antigen of interest, wherein said PBD comprises an amino acid sequence selected from the group consisting of (i) a LysM domain, (ii) an amino acid sequence retrieved from a homology search in an amino acid sequence database with a LysM domain in the C-terminus of AcmA LysM domain and (iii) a sequence showing at least 70% sequence identity to an AcmA LysM domain, provided that the PBD is capable of attaching the substance to the cell wall of a Gram-positive microorganism. Also provided is the use of an antigen-loaded immunogenic carrier complex for the delivery of an (protective) antigen of interest to the immune system of a subject, preferably a human subject. Delivery to the immune system preferably comprises antigen delivery to a mucosal site, such as intranasal delivery, e.g. by means of a spray, or oral, vaginal or rectal delivery.

In a preferred embodiment, the invention provides a subunit vaccine based on an immunogenic carrier complex disclosed herein. Subunit vaccines are vaccines developed against individual viral or bacterial components, also referred to as "immunogenic determinants' that play a key role in eliciting protective immunity. In order to develop subunit vaccines, it is important to identify those components (often (glyco)proteins) of the pathogen that are important for inducing protection and eliminate the others. Some proteins, if included in the vaccine, may be immunosuppressive, whereas in other cases immune responses to some proteins may actually enhance disease. Combining genomics with our understanding of pathogenesis, it is possible to identify specific proteins from most pathogens that are critical in inducing the immune responses (see WO2004/102199). In addition to using a whole protein as a vaccine, it is possible to identify individual epitopes within these protective proteins and develop peptide vaccines. The potential advantages of using subunits as vaccines are the increased safety and less antigenic competition since only a few components are included in the vaccine, ability to target the vaccines to the site where immunity is required, and the ability to differentiate vaccinated animals from infected animals (marker vaccines). One of the disadvantages of subunit vaccines known in the art is that they generally require strong adjuvants and these adjuvants often induce tissue reactions. An immunogenic carrier complex as disclosed herein has built-in immunostimulatory properties and can efficiently deliver antigenic determinants as a particle to immunoreactive sites. Especially GEM particles are readily bound by and/or taken up by specific cells or tissues. The ability of GEMs to target macrophages or dendritic cells enhances their functional efficacy. In fact, it is now possible to mimic a pathogen with respect to its antigenic components while avoiding the undesired effects of other components while maintaining the adjuvant properties. Of course, an immunogenic carrier can be provided with multiple polypeptides. Some of these polypeptides being hybrid antigen-Protan fusions (e.g. as described in WO 99/25836 and WO 02/101026) and some being bifunctional Protan fusions as disclosed herein, each comprising at least one ABD (see FIG. 1). The use of polypeptides with distinct ABDs allows the binding of distinct antigens of interest to a single immunogenic carrier. The use of multiple ABDs, being part of a single polypeptide or of distinct polypeptides, allows for the preparation of multiple epitope vaccines.

In a further aspect, the invention relates to a diagnostic method comprising the use of an immunogenic carrier complex according to the invention. Also provided is a diagnostic kit comprising the use of an immunogenic carrier complex according to the invention. The ABD can be used to capture and immobilize an antigen of interest in a sample, e.g. a biological sample, onto the carrier complex. This 'loaded' carrier complex is suitably used to separate the antigen of interest from the remainder of the sample, for example by centrifugation. Subsequently, the amount of carrier-associated antigen of interest can be detected or quantitated. Thus, the immunogenic carrier complex, for instance a GEM particle, can be used as "biological affinity bead" to isolate an antigen of interest, optionally followed by analysis of the antigen of interest.

The invention is illustrated by the examples below.

LEGENDS TO THE FIGURES

FIG. 1. Schematic Presentation of the Vaccine Delivery Technology of the Invention.

Shown on the right is an immunogenic GEM particle loaded with several different antigens bound to the particle through the use of antigen-Protan fusion proteins and/or bifunctional polypeptides comprising an antigen binding domain (ABD) and a peptidoglycan binding domain (PBD), in this case Protan.

Figure 2:
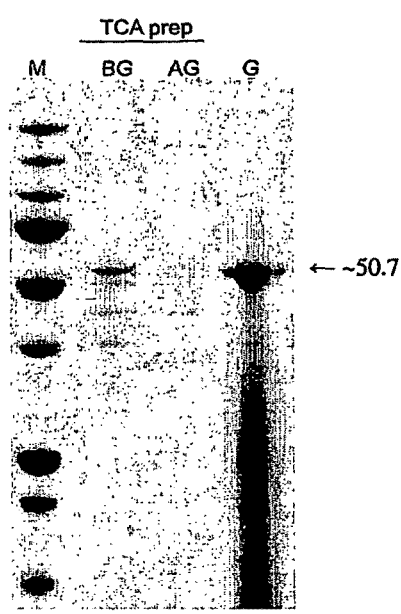

FIG. 2. GEM-binding analysis of the Prota-Protan Bifunctional Polypeptide.

M=Molecular weight marker prestained Precision Plus All Blue (BioRad)

BG=TCA precipitation of ProtA-Protan production medium before binding to GEM particles (200 μl supernatant)

AG=TCA precipitation of production medium after binding to and removal of GEM particles (200 μl supernatant)

G=GEM particles loaded with ProtA-Protan (0.4 unit GEM with 800 μl supernatant)

The arrow indicates the expected migration position of the ProtA-Protan fusion protein (50.7 kilodalton [kDa]).

Figure 3:
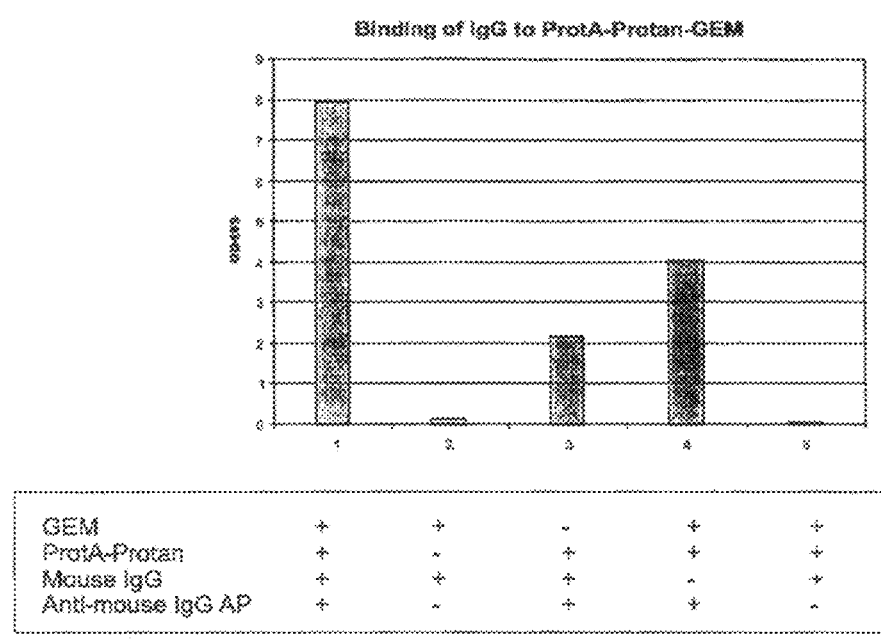

FIG. 3. Binding of Mouse IgG to GEM Particles with Attached ProtA-Protan.

Upper part: Colorimetric values obtained due to the activity of alkaline phosphatase (AP). AP is conjugated to a secondary antibody that recognizes mouse IgG. Thus, if mouse IgG is bound, AP activity can be detected.

Lower part: description of the sample composition of the corresponding samples in the upper part.

Figure 4:
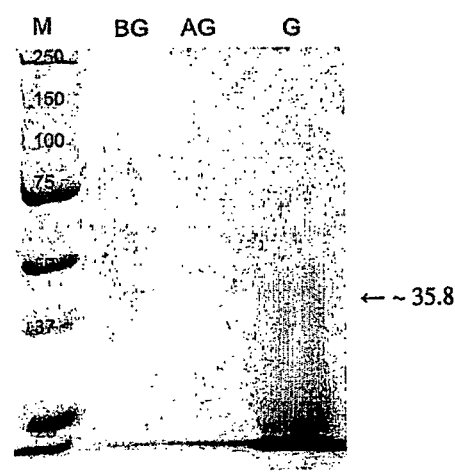

FIG. 4. GEM-Binding Analysis of Streptavidin-Protan

M=Molecular weight marker prestained Precision Plus All Blue (BioRad)

BG=TCA precipitation of Streptavidin-Protan containing medium before binding to GEM particles (200 μl supernatant)

AG=TCA precipitation of medium after binding to and removing of GEM particles (200 μl supernatant)

G=GEM particles loaded with Streptavidin-Protan (0.4 unit GEM with 800 μl supernatant)

The arrow indicates the expected migration position of the Streptavidin-Protan fusion protein (35.8 kDa).

Figure 5:
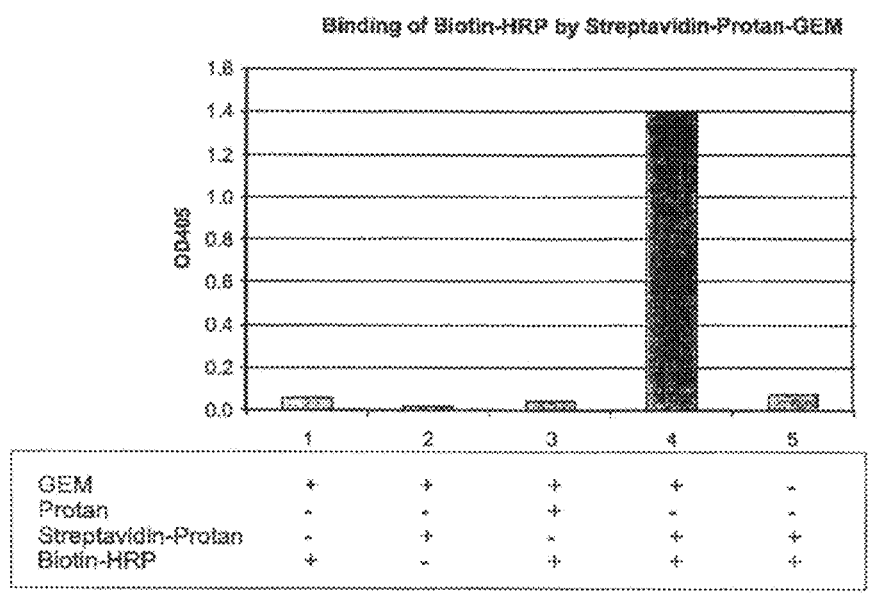

FIG. 5. Binding of Biotin-HRP to GEM Particles with Attached Streptavidin-Protan.

Upper part: the graphic shows the colorimetric values that are obtained due to the activity of horse radish peroxidase (HRP). Biotin is conjugated to HRP. Thus, if biotin is bound, HRP activity will be measured.

Lower part: describes the sample composition of the corresponding samples in the upper part of the figure.

If no Streptavidin-Protan fusion is present (sample 1 and 3), only Protan is present on the GEM particles (sample 3), no Biotin-HRP (sample 2) or GEM particles (sample 5) are added: no activity is measured as expected. Activity is only measured in sample 4, which means that Streptavidin-Protan on the GEM particles binds the Biotin-HRP conjugate. In conclusion, the Streptavidin-Protan bifunctional linker can be attached to GEM particles and this complex can bind biotinylated compounds.

EXPERIMENTAL SECTION

Example 1

Loading of Antibodies on GEM Particles

This example describes the preparation of an antigen binding immunogenic carrier complex using GEM particles as immunogenic carrier and Protein A as antigen binding domain to attach antibodies as antigen of interest to the carrier complex.

Protein A (ProtA) of *Staphylococcus aureus* is a 42 kDa protein that binds to the Fc region of IgG antibodies. It can be used to capture antibodies from a solution and immobilize them on a surface. Here we made a genetic fusion of ProtA with the peptidoglycan binding domain (cA) of the *L. lactis* cell wall hydrolase AcmA comprising three AcmA LysM domains, also herein referred to as protein anchor or 'Protan liner'. The resulting ProtA-Protan bifunctional linker was expressed and secreted by recombinant *L. lactis*. After removal of the recombinant producer cells, the bifunctional linker was attached to lactococcal GEM particles by the Protan moiety in the hybrid linker. The ProtA moiety in the same hybrid linker was still able to bind IgG antibodies, thereby immobilizing these on the GEM particles.

Bacterial Strains and Growth Conditions

The bacterial strains used in this study are listed in Table 1. *L. lactis* strains were grown in 30° C. in M17 broth (DIFCO) as standing cultures or on M17 plates containing 1.5% agar. All media were supplemented with 0.5% glucose (w/v) (GM17) and, when necessary, supplemented with 5 μg/ml chloramphenicol (SIGMA) for plasmid selection. Induction for $P_{nisA}$-driven gene expression was done with the culture supernatant of the nisin producing *L. lactis* strain NZ9700 as described previously (Kuipers et al. [1997] Trends Biotechnol. 15:135-140).

TABLE 1

Bacterial strains and plasmids

| | Relevant phenotype or genotype | Reference or origin |
|---|---|---|
| Strain | | |
| *Lactococcus lactis* subsp. *cremoris* | | |
| PA1001 | Derivative of the strain NZ9000 (MG1363 pepN::nisRK) carrying a 701-bp SacI/SpeI deletion in acmA and a complete deletion of htrA | Steen et al. [2003] J. Biol. Chem. 278: 23874-23881. |
| NZ9700 | Nisin-producing transconjugant containing the nisin-sucrose transposon Tn5276 | Kuipers et al.[1997] Trends Biotechnol. 15: 135-140) |
| Plasmids | | |
| pPA3 | $cm^R$, pNZ8048 derivative containing the Protan domain under control of $P_{nisA}$ | Steen et al. [2003] J. Biol. Chem. 278: 23874-23881. |
| pPA217 | $cm^R$, pPA3 containing Protein A fusion to the Protan domain under control of $P_{nisA}$ | Example 1 |
| pPA218 | $cm^R$, pPA3 containing Streptavidin core fusion to the Protan domain under control of $P_{nisA}$ | Example 2 |

$cm^R$: chloramphenicol resistance gene.
$P_{nisA}$: nisA promoter.

General Molecular Biology

Enzymes and buffers were purchased from New England Biolabs or Fermentas. Electro-transformation of *L. lactis* was carried out as described previously (Holo and Nes [1995] Methods Mol. Biol. 47:195-199) using a Bio-Rad Gene Pulser (Bio-Rad). Nucleotide sequence analyses were performed by BaseClear (Leiden, The Netherlands).

Production of the Fusion Construct Containing ProtA-Protan

ProtA (NCBI accession number BAB93949.1; U.S. Pat. No. 5,151,350; Uhlen et al. [1984] J. Biol. Chem. 259:1695-1702) from *S. aureus* contains five homologous IgG-Fc binding regions consisting of approximately 58 amino acids each. For the fusion of ProtA to Protan, only the Fc binding domains were amplified by PCR using primers SpA.fw and SpA.rev (see Table 2).

TABLE 2

Primers used in this study

| Name | Sequence (5'→3') | Restriction site |
|---|---|---|
| SpA.fw | CC<u>GTCTC</u>CCATGGTTGCTGATGCGCAACA AAATAAC (SEQ ID NO: 3) | Esp3I (underlined, resulting in <u>NcoI</u> sticky end) |
| SpA.rev | CC<u>GTCTC</u>GAATTCGTTTTGGTGCTTGAGC ATCG (SEQ ID NO: 4) | Esp3I (underlined, resulting in <u>EcoRI</u> sticky end) |

After amplification of the Fc-binding part from the *S. aureus* genome, the 710 bp PCR fragment was isolated from gel and digested with Esp3I, resulting in NcoI and EcoRI sticky ends. The digested product was ligated into pPA3 which was digested with EcoRI and NcoI. The ligation mixture was transferred by electroporation to *L. lactis* PA1001 and resulted in plasmid pPA217. Strain *L. lactis* (pPA217) produces secreted ProtA-Protan polypeptide.

TCA Precipitation of Produced Fusion Proteins

For detection of the amount of produced polypeptide in the cell free culture medium, a TCA precipitation was performed. This was done by addition of 200 µl 50% trichloroacetic acid TCA) to 1 ml of cell free culture medium containing the Protan fusion protein. The mixture was placed on ice for 1 hour after vortexing. The precipitated protein was spun down in a centrifuge for 20 minutes at 14,000 rpm (4° C.), was washed with acetone, dried in a vacuum exicator and resuspended in SDS sample buffer.

GEM Production and Binding Conditions

Chemical pre-treatment of *L. lactis* NZ9000 for the production of GEM, was routinely done with hydrogen chloride (HCl, pH 1.0) as follows: cells of stationary phase cultures were collected by centrifugation and washed once with 0.5 volume of phosphate-buffered saline (PBS: 58 mM $Na_2HPO_4$, 17 mM $Na_2H_2PO_4$, 68 mM NaCl, pH 7.2). Cells were resuspended in $\frac{1}{5}^{th}$ volume of HCl, pH1.0 solution and boiled for 30 min. Subsequently, the GEM particles formed in this way were washed three times with PBS, and resuspended in PBS until an average of $2.5 \times 10^{10}$ GEM particles/ml as was determined with a Burker-Turk hemocytometer. GEM particles were either immediately used for binding experiments or stored in 1.0 ml aliquots at −80° C. until use.

In a typical binding experiment $2.5 \times 10^9$ GEM particles (1 unit) were incubated for 30 min at room temperature in an over-end rotator with 2 ml of cell-free culture medium containing a bifunctional polypeptide (Protan fusion protein). After binding, GEM particles were collected by centrifugation, washed twice with PBS and analyzed by SDS-PAGE or enzymatic activity.

AP Enzyme Assay

Enzyme activity of bound rabbit anti-mouse IgG Alkaline Phosphatase (AP) (Sigma) was measured colorimetrically. 0.5 unit GEM particles loaded with the fusion protein ProtA-Protan, mouse IgG1 (kappa light chain) (Sigma) (1 ml 1:100 dilution in PBS) and rabbit anti-mouse IgG AP (Sigma) (1 ml 1:10,000 dilution in PBS) were spun down and washed twice with PBS. Alkaline phosphatase activity was determined by incubating the loaded GEM particles in 1 ml 4-nitro phenylphosphate (Sigma) (1 mg/ml in 50 mM sodium carbonate buffer, pH 9.6, 1 mM $MgCl_2$) at room temperature. After 5 min, the reaction was stopped by addition of 0.5 ml 2M NaOH. GEM particles were spun down, and the absorbance of the supernatant at 405 nm was measured by a spectrophotometer (BioRad Smartspec 300).

Attaching of the ProtA-Protan Polypeptide to GEM Particles

Production of the polypeptide was induced as described above. After overnight induction, the expression of the protein was tested by performing a GEM-binding assay with 1 ml supernatant of the producing strain to 0.5 U of GEM. The results are given in FIG. 2. It is clear that most of the produced ProtA-Protan fusion peptide (lane BG) is specifically removed from the production medium (lane AG) and binds efficiently to the GEM particles (lane G). The smear in lane G is caused by the degraded *L. lactis* proteins present in the GEM particles.

Mouse IgG Binding to ProtA-Protan-GEM Particles

The antibody-binding activity of the ProtA-Protan polypeptide attached to GEM particles was tested using the reported enzyme alkaline phosphatase (AP) as described above. For this experiment different control groups were taken into account, as described in FIG. 3. The results clearly demonstrate that mouse-IgG binds to GEM particles that are activated with attached ProtA-Protan fusion protein (sample 1). No activity was detected when no ProtA-Protan was added to the GEM particles (sample 2) or when no secondary antibody with conjugated AP was added (sample 5), as expected. The anti-mouse secondary antibody that contains the conjugated AP is also an IgG antibody and binds as well to the ProtA-Protan-GEM complex even in the absence of mouse IgG (sample 4). In the absence of GEM particles some activity is measured (sample 3), most likely due to some aggregation of the ProtA-Protan fusion that is spun down during the procedure or due to some a specific binding of the protein to the plastic reaction tube. In conclusion, the ProtA-Protan bifunctional linker can be attached to GEM particles and this complex can bind IgG antibodies.

In conclusion, the ProtA-Protan bifunctional polypeptide can be attached to GEM particles to yield an immunogenic carrier complex and this complex can be loaded with IgG antibodies.

Example 2

Immobilization of biotinylated compounds on GEM particles

Streptavidin of *Streptomyces avidinii* is a 15 kDa protein that is functional as a tetramer and binds biotin. It can be used as antigen binding domain (ABD) to capture biotinylated substances from a solution and immobilize them on a surface. Here we made a genetic fusion of Streptavidin with the Protan linker described in Example 1. The resulting Streptavidin-Protan bifunctional polypeptide was expressed and secreted by recombinant *L. lactis*. After removal of the recombinant producer cells, the bifunctional linker was attached to lactococcal GEM particles by the peptidoglycan binding domain (PBD) of the Protan moiety of the polypeptide. The ABD in the same polypeptide was still functional and was used to bind to and immobilize biotinylated horse radish peroxidase as antigen of interest on the GEM particles.

Bacterial strain, plasmids and procedures for growth conditions, general molecular biology techniques, GEM production and binding conditions and TCA precipitation of produced fusion proteins were the same as in Example 1.

HRP Enzyme Assay

Enzyme activity of bound Biotin-Horseradish Peroxidase (HRP) (Molecular Probes) was measured colorimetrically. 0.5 U GEM particles loaded with the fusion protein Streptavidin-Protan and Biotin-HRP (1 ml 1:2000 Biotin-HRP (1 mg/ml) in PBS) were spun down and washed twice with PBS. Horse radish peroxidase activity was determined by incubating the loaded GEM particles in 1 ml ABTS (Fluka) (10 mg in 100 ml 0.05 M phosphate-citrate buffer pH 5.0) and 1 µl $H_2O_2$ (100%) at room temperature. After 5 min, the reaction was stopped by addition of 100 µl 10% SDS. GEM particles were spun down, and the absorbance of the supernatant at 405 nm was measured by a spectrophotometer (BioRad Smartspec 300).

Production of the Fusion Construct Containing Streptavidin-Protan

Only the core of Streptavidin was used as ABD for the production of the bifunctional polypeptide (Streptavidin-Protan). This core is the biotin binding unit of Streptavidin (NCBI accession number CAA00084), containing amino acids $A_{37}$-$S_{163}$. (Argaraña et al. [1986] Nucleic Acid Research 14:1871-1882, Pähler et al. [1987] J. Biol. Chem. 262: 13933-13937). For the fusion of Streptavidin core to the Protan moiety comprising the PBD, 8 primers were designed. These primers could be amplified to each other, first Strep1.fw until Strep4.rev and Strep5.fw until Strep8.rev in two different PCR reactions. The two PCR products were mixed and amplified with the two exterior primers Strep1.fw and Strep8.rev in which a streptavidin-core gene-fragment of 397 bp was produced that was optimized for *L. lactis* codon usage. The primers used for the production of this gene fragment are described in Table 3.

To be able to screen the PCR fragment for containing the correct DNA sequence, the Zero Blunt® TOPO® Cloning Kit (Invitrogen) was used. The Zero Blunt® TOPO® plasmid containing the correct streptavidin-core gene fragment was digested with EcoRI and NcoI. This digestion product was ligated into pPA3 which was also digested with EcoRI and NcoI. The ligation mixture was transferred by electroporation to *L. lactis* PA1001 and resulted in plasmid pPA218. Strain *L. lactis* (pPA218) produced and secreted Streptavidin-Protan polypeptide in the culture medium.

Attaching the Polypeptide to Immunogenic Carrier

Production of the fusion protein was induced as described above. After overnight induction, the expression of the protein was tested by performing a GEM-binding assay with 1 ml supernatant of the producing strain to 0.5 unit of GEM particles (FIG. 4). It is clear that most of the produced Streptavidin-Protan fusion (lane BG) is specifically removed from the production medium Lane AG) and binds efficiently to the GEM particles (lane G). The smear in lane G is caused by the degraded *L. lactis* proteins present in the GEM particles.

TABLE 3

Primers used for production of streptavidin core gene. The nucleotide stretches which are either in italics, underlined, double underlined, in lower case letters, in italics and underlined, in lower case letters and underline or in lower case letters and in italics and underlined can anneal to each other.

| Name | Sequence (5'→3') Restriction sites are written in bold | Restriction site |
|---|---|---|
| Strep1.fw (SEQ ID NO: 5) | TATCCATGGTT GCA GAA GCA GGT ATT ACA GGT ACA TGG TAT AAT CAA CTT *GGT TCA ACA TTT* | NcoI |
| Strep2.rev (SEQ ID NO: 6) | ACC AAC AGC TGA TTC ATA TGT TCC TGT AAG AGC ACC ATC *AGC ACC AGC TGT AAC AAT AAA TGT* | NdeI |
| Strep3.fw (SEQ ID NO: 7) | CTT ACA GGA ACA TAT GAA TCA GCT GTT GGT AAT | NdeI |
| Strep4.rev (SEQ ID NO: 8) | *CAGT CCAACC AAG AGC* GGT ACC ACT ACC GTC TGT AGC TGG Agc act atc ata acg acc agt gag aac | KpnI |
| Strep5.fw (SEQ ID NO: 9) | *AGT* GGT ACC *GCT CTT GGT TGG ACT G*TT GCA TGG | KpnI |
| Strep6.rev (SEQ ID NO: 10) | aag aag cca ttg tgt att aat tct agc TTC AGC ACC ACC AAC ATA TTG ACC act cca aat tgt aac tta ata aac att | — |
| Strep7.fw (SEQ ID NO: 11) | gct aga att aat aca caa tgg ctt ctt ACA TCA GGT ACA ACT | — |
| Strep8.rev (SEQ ID NO: 12) | GGAATTCT TGA TGC AGC TGA TGG TTT AAC TTT AGT AAA TGT ATC ATG ACC AAC AAG AGT TGA TTT | EcoRI |

Biotin-HRP Binding to Streptavidin-Protan-GEM Particles

The biotin binding activity of the fusion protein bound to GEM was tested as described herein below using HRP as reported enzyme. For this experiment different control groups were taken into account, as described in FIG. 5. If no Streptavidin-Protan fusion is present (sample 1 and 3), only Protan is present on the GEM particles (sample 3), no Biotin-BRP (sample 2) or GEM particles (sample 5) are added, no activity is measured as expected. Activity is only measured in sample 4 which means that Streptavidin-Protan on the GEM particles binds the Biotin-HRP conjugate.

In conclusion, the Streptavidin-Protan bifunctional polypeptide can be attached to immunogenic GEM particles and this complex can bind a biotin-modified antigen of interest.

Example 3

Immobilization of Inactivated Whole Poliovirus on GEM Particles Using Bifunctional Protan Linkers Phage display (Smith and Petrenko [1997] Chem. Rev. 97:391-410) has emerged as a powerful technique for the selection of specific binding peptides (Sidhu et al. [2000] Meth. Enzymol. 328:333-344; Cwirla et al. [1990] Proc. Natl. Acad. Sci. USA. 87:6378-6382). A DNA sequence encoding the peptide is translationally fused to DNA encoding the gene 3 minor coat protein, yielding display of the peptide on the surface of the phage. In this way a physical linkage was established between the displayed peptide and the DNA encoding this peptide. Phage peptide libraries can be used to efficiently search for specific binders out of a pool of variants by selection on a specific target, a process called panning. Selected phage can subsequently be amplified in *Escherichia coli* and subjected to additional rounds of panning to enrich peptides that specifically bind to the target.

Random peptide libraries has been used in various applications such as binding to proteins (Sidhu et al. [2000] Meth. enzymol. 328:333-344), polysaccharides Kim et al. [2005] Biochem. Biophys. Res. Commun. 329:312-317), bacterial spores Knurr et al. [2003] Appl. Environ. Microbiol. 69:6841-6847), whole cells (Brown [2000] Curr. Opinion. Chem. Biol. 4:16-21), and inorganic materials (Whaley et al [2000] Nature 405:665-668).

In the current application phage display can be used for the selection of specific binding peptides that are subsequently used for the construction of bifunctional Protan linkers. Application of the bifunctional polypeptides like Protan linkers allows the non-covalent attachment of a compound of interest, i.e. proteins, polysaccharides, bacteria, viruses, or fungi to GEM particles. Peptides are advantageous over binding proteins in that they are less immunogenic, and easy to produce. In this Example we describe the construction of a phagemid-based peptide library which was used for the selection of specific binding peptides targeted to inactivated whole poliovirus. Selected peptides that specifically bind to whole poliovirus were genetically fused to Protan and the bifunctional Protan linkers were attached to lactococcal GEM particles. This allows the non-covalent coupling of inactivated whole poliovirus. The resulting antigen-loaded immunogenic carrier complex of GEM particle with inactivated whole poliovirus is directly applicable in vaccines.

Construction of Peptide Phage Display Vector

The phagemid PPEP is constructed from pCANTAB 5EST (Amersham Pharmacia) for the display of short peptide sequences. The display of peptides requires the in frame fusion of peptides to the minor coat protein 3 (g3p) of phage M13. Therefore, superfluous nucleotide sequences in pCANTAB 5EST between the HindIII and BamHI recognition sequence are removed and replaced by a PCR-assembled fragment encoding only the relevant sequence elements. In addition, KpnI and BpiI recognition sequences are introduced to allow cloning of peptide sequences at the 5'-end of gene 3. Furthermore, in order to improve the target accessibility of a displayed peptide a small spacer sequence of three glycine residues is included between the cloned peptide and the minor coat protein.

The construction of the peptide phage display vector involves a number of polymerase chain reaction (PCR) steps. First, a DNA fragment from the HindIII recognition sequence until the start of gene 3 is synthesized by two successive overlap PCRs. A temporary assembly PCR product is produced from oligonucleotides Cb1F2.fw, 5'-ggagccttttttttg-gagattttcaacgtgaaaaaattattattc gcaattcctttagtggta; (SEQ ID NO: 13); Cb1F.3.fw, 5'-gcaattcctttagtggtacctttctat-gcggcccagccggccat ggcccagggcgctgggaga;(SEQ ID NO: 14); and Cb1F4.rev, 5'-ttcaacagtaccgccaccccgtcttctc-ccagcgccctgggc (SEQ ID NO: 15). This temporary amplicon is purified and used in a second overlap PCR as template together with the outside primers Cb1F1.fw, 5'-atgattacgc-caagcttt-ggagcttttttttggag (SEQ ID NO: 16)and Cb1F5.rev 5'-aggttttgctaaacaactttcaacagtaccgccacc (SEQ ID NO: 17), yielding the final assembled PCR fragment. A second DNA fragment containing the first 617 nucleotides of gene 3 is produced by PCR using the oligonucleotides Cb2.fw, 5'-act-gttgaaagttgtttagcaaaacct (SEQ ID NO: 18)and Cb2.rev 5'-agacgattggccttgatattcacaaac (SEQ ID NO: 19). In the final overlap PCR, the latter amplicon is combined with the first assembly PCR product and the outside primers Cb1F1.fw and Cb2.rev yielding a 711 bp PCR fragment. This amplification product is digested with HindIII and BamHI and ligated into the same sites of pCANTAB 5EST resulting in phagemid pPEP.

Construction of Random Peptide Libraries

Phagemid pPEP contains KpnI and BpiI recognition sites at the 5' end of gene 3 for display of random peptides as N-terminal g3p fusions. Since pPEP is a phagemid, peptides are displayed in a monovalent format i.e. only one or two copies of g3p on the surface of each phage particle will be fused to the cloned peptide.

A library of oligonucleotides encoding 12-amino acid linear random peptides is constructed according to Noren and Noren (Methods 23:169-178). Briefly, a 92 nucleotide library oligonucleotide, PEP12Lib.rev, is designed with the sequence 5'-accgaagaccccacc(BNN)12ctgggccatggccg-gctgggccgcatagaaaggtacccggg (B=C or G or T) (SEQ ID NO: 20). The universal extension primer PEPext.fw 5'-catgc-ccgggtacctttctatgcgg (SEQ ID NO: 21) is annealed and extended in a Klenow reaction. The resulting double stranded library oligonucleotide is purified, digested with KpnI and BpiI, and ligated into pPEP that had been digested with the same enzymes yielding pPEP12. The ligation mixture is transferred to *E. coli* XL1-blue or TG1 cells (Stratagene) by electroporation until ≈$10^9$ independent clones are obtained. To produce phagemid particles *E. coli* TG1 or XL1 blue cells containing pPEP12 are infected with a 30-fold excess M13K07 helper phage. From the infected culture, phagemid particles are purified by PEG precipitation.

Biopanning

Inactivated whole poliovirus particles are used for affinity selection of specific binding peptides. Poliovirus is captured on ELISA plates coated with rabbit anti-poliovirus IgG (0.5-1 µg/ml). Alternatively, poliovirus is displayed on GEM particles loaded with anti-poliovirus IgG bound to ProtA-Protan fusions (Example 1). Approximately $10^{11}$ phagemid particles in phosphate buffered saline (PBS)+0.1% Tween 20 (PBS-T) from the dodecapeptide library are allowed to react in wells, or with ≈$10^9$ GEMs with the inactivated poliovirus for 1 h at room temperature. After incubation, unbound phages are removed. The GEMs or wells are washed ten times with PBS-T and bound phages are eluted with 0.2 M glycine/HCl (pH 2.2). The eluted phage suspension is neutralized with 2 M Tris base. The eluted phages are used to infect *E. coli* TG1 or XL1 blue cells. A total of 6 cycles of selection are performed, after which individual phage clones are isolated for further analysis.

Binding Analysis

To evaluate binding of peptides to the poliovirus multi-well plates are coated with anti-poliovirus IgG (0.5-1 µl/ml). After washing with PBS-T, the wells are blocked with 1% BSA in PBS-T for 1 h at room temperature. Inactivated whole poliovirus is added in PBS-T+1% BSA, and incubated for 1 h at room temperature. Selected peptide-phages ($10^{10}$ cfu/ml) in PBS-T are added to the wells. After 1 h room temperature the plates are washed three times with PBS-T. Peptide-phages bound to poliovirus are detected with HRP-conjugated anti-M13 antibody (Pharmacia) using ABTS [2,2'-azinobis-(3-ethylbenzothiazoline-6-sulfonic acid)] as a substrate. The absorbance is measured after a suitable time period at 410 nm. Two peptide-phages that show the best binding to the poliovirus are selected for further characterization by sequence analysis. The two phagemids are designated pPEP-PV1 and pPEP-PV2.

Construction of PEP-Protan Fusion Proteins

Based on the nucleotide sequence of the binding peptides in pPEP-PV1 and pPEP-PV2, two complementary oligonucleotides corresponding to binding peptides PV1 and PV2 are designed and produced with BsaI and BpiI overhanging 5'-ends. Equal molar concentrations of both oligonucleotides are annealed in a total volume of 100 μl 10 mM Tris-HCl (pH 8.0). The mixture is heated to 94° C. and slowly cooled to room temperature in a thermal cycler. The annealed oligonucleotides are ligated into pPA224 digested with BsaI and BpiI. Plasmid pPA224 is a derivative of pPA3 (Steen et al. [2003] J. Biol. Chem. 278:23874-23881), which lacks the c-myc sequence and has a modified multiple cloning site between the usp45 signal sequence and the Protan sequence. After ligation the mixtures are transferred to *L. lactis* PA1001 by electroporation. The result are plasmids pPA224PV1 and pPA224-PV2 in which PV1 and PV2, respectively, are transcriptionally fused to the 5'-end of the Protan sequence.

*L. lactis* PA1001(pPA224-PV1) and *L. lactis* PA1001 (pPA224-PV2) secrete PV1-Protan and PV2-Protan bifunctional linkers, respectively, into the growth medium. The producer cells are removed from the production medium by microfiltration and/or centrifugation.

Binding of Inactivated Poliovirus to Antigen-Binding GEM Particles

The bifunctional polypeptides PV1-Protan and PV2-Protan attaches efficiently to lactococcal GEM particles, either each alone or in combination. The antigen-binding immunogenic carrier complexes PV1-Protan-GEM, PV2-Protan-GEM and PV1+PV2-Protan-GEM thus obtained are mixed with a suspension containing inactivated poliovirus particles. In all cases the poliovirus particles efficiently bind to the GEM-bifunctional Protan complexes.

This Example illustrates that specific antigen binding domains can be selected using phage display, even for an entire viral particle and that this binding domain can be used in a bifunctional polypeptide to immobilize the entire virus on an immunogenic carrier.

Furthermore, the examples demonstrate that either known antigen binding domains or newly selected binding domains from a random peptide library can be used in Protan fusions as bifunctional Protan linkers to immobilize a desired compound (e.g. antigen) on GEM particles, without the need to modify the compound of interest before binding to an immunogenic carrier.

The invention claimed is:

1. An antigen-loaded immunogenic carrier complex comprising at least one bifunctional polypeptide attached to an immunogenic carrier, said bifunctional polypeptide comprising a peptidoglycan binding domain (PBD) through which the bifunctional polypeptide is attached to said immunogenic carrier, fused to an antigen binding domain (ABD) that non-covalently binds an antigen of interest, wherein said PBD comprises a LysM domain, provided that the PBD is able to attach to the cell wall of a Gram-positive microorganism; and
   wherein at least one antigen of interest is non-covalently bound to said ABD.

2. The antigen-loaded immunogenic carrier complex according to claim 1, wherein at least two bifunctional polypeptides are attached to said immunogenic carrier, each bifunctional polypeptide having a distinct ABD and distinct antigen of interest.

3. The antigen-loaded immunogenic carrier complex according to claim 1, wherein said immunogenic carrier comprises a non-viable spherical peptidoglycan particle obtained from a Gram positive bacterium (GEM particle).

4. The antigen-loaded immunogenic carrier complex of claim 3, wherein said bacterium is a non pathogenic bacterium.

5. The antigen-loaded immunogenic carrier complex of claim 4, wherein said bacterium is selected from the group consisting of a *Lactococcus*, a *Lactobacillus*, a *Bacillus* and a *Mycobacterium* ssp.

6. The antigen-loaded immunogenic carrier complex according to claim 1, wherein said peptidoglycan binding domain (PBD) comprises the C-terminal peptidoglycan binding domain of the *Lactococcus lactis* cell wall hydrolase AcmA.

7. The complex antigen-loaded immunogenic carrier according to claim 1, wherein said ABD binds an antigen selected from the group consisting of polypeptides, carbohydrates, lipids, polynucleotides, pathogenic antigens, inactivated viral particles, and purified antigenic determinants.

8. A method for providing the antigen-loaded immunogenic carrier complex according to claim 1, comprising the steps of:
provide an immunogenic carrier;
providing a bifunctional polypeptide comprising a peptidoglycan binding domain (PBD) fused to an antigen binding domain (ABD) allowing attachment of said polypeptide to said immunogenic carrier;
contacting said immunogenic carrier and said bifunctional polypeptide; and
contacting said bifunctional polypeptide with an antigen of interest so as to produce an antigen-loaded immunogenic carrier complex.

9. The method according to claim 8, wherein providing an immunogenic carrier comprises preparing non-viable, spherical peptidoglycan particles from a Gram-positive bacterium.

10. The method according to claim 8, wherein providing said bifunctional polypeptide comprises selecting an antigen binding domain from a random peptide or antibody library or by utilizing a phage display technology.

11. The method according to claim 8, comprising producing the bifunctional polypeptide in a host cell by recombinant expression of a nucleic acid construct encoding said bifunctional polypeptide.

12. The method according to claim 11, wherein said host cell secretes the bifunctional polypeptide in the culture medium.

13. A pharmaceutical composition comprising the antigen-loaded immunogenic carrier complex of claim 1.

14. An immunogenic composition comprising the pharmaceutical composition of claim 13.

15. The antigen-loaded immunogenic carrier complex of claim 2, wherein the immunogenic carrier comprises a non-viable spherical peptidoglycan particle obtained from a Gram positive bacterium (GEM particle).

16. The antigen-loaded immunogenic carrier complex of claim 15, wherein the Gram positive bacterium is non pathogenic in a selected subject.

17. The antigen-loaded immunogenic carrier complex of claim 15, wherein the Gram positive bacterium is a food-grade bacterium.

18. An antigen-loaded immunogenic carrier complex comprising:
a bifunctional polypeptide comprising:
an antigen binding domain non-covalently bonded to an antigen of interest, said antigen binding domain fused to
a peptidoglycan binding domain through which the bifunctional polypeptide is attached to the antigen-loaded immunogenic carrier, said peptidoglycan binding domain comprising
a LysM domain,
wherein the peptidoglycan binding domain is able to attach to the cell wall of a Gram-positive microorganism.

19. An antigen-loaded immunogenic carrier complex comprising at least one bifunctional peptide attached to an immunogenic carrier, said bifunctional peptide comprising a peptidoglycan binding domain (PBD) through which the bifunctional peptide is attached to the immunogenic carrier, fused to an antigen binding domain (ABD) that non-covalently binds an antigen of interest, wherein the PBD comprises a LysM domain, provided that the PBD is able to attach to the cell wall of a Gram-positive microorganism; and
wherein at least one antigen of interest is non-covalently bound to the ABD.

* * * * *

SEQUENCE LISTING

```
<160> NUMBER OF SEQ ID NOS: 21

<210> SEQ ID NO 1
<211> LENGTH: 7
<212> TYPE: PRT
<213> ORGANISM: Artificial sequence
<220> FEATURE:
<223> OTHER INFORMATION: random heptamer

<400> SEQUENCE: 1

Ala Trp Leu Pro Trp Ala Lys
1               5

<210> SEQ ID NO 2
<211> LENGTH: 7
<212> TYPE: PRT
<213> ORGANISM: Artificial sequence
<220> FEATURE:
<223> OTHER INFORMATION: Random heptamer

<400> SEQUENCE: 2

Asn Leu Gln Glu Phe Leu Phe
1               5

<210> SEQ ID NO 3
<211> LENGTH: 36
<212> TYPE: DNA
<213> ORGANISM: Artificial sequence
<220> FEATURE:
<223> OTHER INFORMATION: pcr primer

<400> SEQUENCE: 3
ccgtctccca tggttgctga tgcgcaacaa aataac                                 36
```

<210> SEQ ID NO 4
<211> LENGTH: 33
<212> TYPE: DNA
<213> ORGANISM: Artificial Sequence
<220> FEATURE:
<223> OTHER INFORMATION: pcr primer

<400> SEQUENCE: 4
ccgtctcgaa ttcgttttgg tgcttgagca tcg                           33

<210> SEQ ID NO 5
<211> LENGTH: 78
<212> TYPE: DNA
<213> ORGANISM: artificial sequence
<220> FEATURE:
<223> OTHER INFORMATION: pcr primer Nco I restriction site

<400> SEQUENCE: 5
tatccatggt tgcagaagca ggtattacag gtacatggta taatcaactt ggttcaacat    60
ttattgttac agctggtg                                           78

<210> SEQ ID NO 6
<211> LENGTH: 69
<212> TYPE: DNA
<213> ORGANISM: Artificial sequence
<220> FEATURE:
<223> OTHER INFORMATION: PCR primer Nde I site

<400> SEQUENCE: 6
accaacagct gattcatatg ttcctgtaag agcaccatca gcaccagctg taacaataaa    60
tgttgaacc                                                     69

<210> SEQ ID NO 7
<211> LENGTH: 74
<212> TYPE: DNA
<213> ORGANISM: Artificial sequence
<220> FEATURE:
<223> OTHER INFORMATION: pcr primer Nde I

<400> SEQUENCE: 7
cttacaggaa catatgaatc agctgttggt aatgctgaaa gtcgttatgt tctcactggt    60
cgttatgata gtgc                                               74

<210> SEQ ID NO 8
<211> LENGTH: 67
<212> TYPE: DNA
<213> ORGANISM: Artificial sequence
<220> FEATURE:
<223> OTHER INFORMATION: pcr primer Kpn I site

<400> SEQUENCE: 8
cagtccaacc aagagcggta ccactaccgt ctgtagctgg agcactatca taacgaccag    60
tgagaac                                                       67

<210> SEQ ID NO 9
<211> LENGTH: 75
<212> TYPE: DNA
<213> ORGANISM: Artificial sequence
<220> FEATURE:
<223> OTHER INFORMATION: pcr primer Kpn I -continued

```
<400> SEQUENCE: 9
agtggtaccg ctcttggttg gactgttgca tggaaaaata attatcgtaa tgctcattca    60
gctacaactt ggagt                                                     75

<210> SEQ ID NO 10
<211> LENGTH: 78
<212> TYPE: DNA
<213> ORGANISM: artificial sequence
<220> FEATURE:
<223> OTHER INFORMATION: primer

<400> SEQUENCE: 10
aagaagccat tgtgtattaa ttctagcttc agcaccacca acatattgac cactccaaat    60
tgtaactaaa taaacatt                                                  78

<210> SEQ ID NO 11
<211> LENGTH: 75
<212> TYPE: DNA
<213> ORGANISM: Artificial sequence
<220> FEATURE:
<223> OTHER INFORMATION: primer

<400> SEQUENCE: 11
gctagaatta atacacaatg gcttcttaca tcaggtacaa ctgaagctaa tgcttggaaa    60
tcaactcttg ttggt                                                     75

<210> SEQ ID NO 12
<211> LENGTH: 74
<212> TYPE: DNA
<213> ORGANISM: Artificial sequence
<220> FEATURE:
<223> OTHER INFORMATION: primer EcoRI

<400> SEQUENCE: 12
ggaattcttg atgcagctga tggtttaact ttagtaaatg tatcatgacc aacaagagtt    60
gatttccaag catt                                                      74

<210> SEQ ID NO 13
<211> LENGTH: 63
<212> TYPE: DNA
<213> ORGANISM: artificial sequence
<220> FEATURE:
<223> OTHER INFORMATION: primer

<400> SEQUENCE: 13
ggagcctttt ttttggagat tttcaacgtg aaaaaattat tattcgcaat tcctttagtg    60
gta                                                                  63

<210> SEQ ID NO 14
<211> LENGTH: 63
<212> TYPE: DNA
<213> ORGANISM: artificial sequence
<220> FEATURE:
<223> OTHER INFORMATION: primer

<400> SEQUENCE: 14
gcaattcctt tagtggtacc tttctatgcg gcccagccgg ccatggccca gggcgctggg    60
aga                                                                  63
```

```
<210> SEQ ID NO 15
<211> LENGTH: 42
<212> TYPE: DNA
<213> ORGANISM: artificial sequence
<220> FEATURE:
<223> OTHER INFORMATION: primer

<400> SEQUENCE: 15
ttcaacagta ccgccacccc gtcttctccc agcgccctgg gc                            42

<210> SEQ ID NO 16
<211> LENGTH: 36
<212> TYPE: DNA
<213> ORGANISM: Artificial sequence
<220> FEATURE:
<223> OTHER INFORMATION: primer

<400> SEQUENCE: 16
atgattacgc caagctttgg agcctttttt ttggag                                  36

<210> SEQ ID NO 17
<211> LENGTH: 36
<212> TYPE: DNA
<213> ORGANISM: artificial sequence
<220> FEATURE:
<223> OTHER INFORMATION: primer

<400> SEQUENCE: 17
aggttttgct aaacaacttt caacagtacc gccacc                                  36

<210> SEQ ID NO 18
<211> LENGTH: 27
<212> TYPE: DNA
<213> ORGANISM: artificial sequence
<220> FEATURE:
<223> OTHER INFORMATION: primer

<400> SEQUENCE: 18
actgttgaaa gttgtttagc aaaacct                                            27

<210> SEQ ID NO 19
<211> LENGTH: 27
<212> TYPE: DNA
<213> ORGANISM: artificial sequence
<220> FEATURE:
<223> OTHER INFORMATION: primer

<400> SEQUENCE: 19
agacgattgg ccttgatatt cacaaac                                            27

<210> SEQ ID NO 20
<211> LENGTH: 92
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
```

```
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 20
accgaagacc ccaccbnnbn nbnnbnnbnn bnnbnnbnnb nnbnnbnnbn nctgggccat      60
ggccggctgg gccgcataga aaggtacccg gg                                   92

<210> SEQ ID NO 21
<211> LENGTH: 25
<212> TYPE: DNA
<213> ORGANISM: artificial sequence
<220> FEATURE:
<223> OTHER INFORMATION: primer

<400> SEQUENCE: 21
catgcccggg tacctttcta tgcgg                                           25
```